United States Patent
Petersen (10) Patent No.: US 11,026,662 B2
(45) Date of Patent: Jun. 8, 2021

(54) ULTRASOUND TRANSMIT/RECEIVE FOR PULSE INVERSION

(71) Applicant: Siemens Medical Solutions USA, Inc., Malvern, PA (US)

(72) Inventor: David A. Petersen, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 593 days.

(21) Appl. No.: 15/868,733

(22) Filed: Jan. 11, 2018

(65) Prior Publication Data

US 2019/0209139 A1 Jul. 11, 2019

(51) Int. Cl.
*A61B 8/00* (2006.01)
*A61B 8/08* (2006.01)
*A61B 8/12* (2006.01)
*G01S 15/89* (2006.01)

(52) U.S. Cl.
CPC .............. *A61B 8/54* (2013.01); *A61B 8/0883* (2013.01); *A61B 8/12* (2013.01); *A61B 8/4488* (2013.01); *A61B 8/52* (2013.01); *A61B 8/5207* (2013.01); *G01S 15/89* (2013.01)

(58) Field of Classification Search
CPC ....... A61B 8/54; A61B 8/5207; A61B 8/0883; A61B 8/52; A61B 8/4488; A61B 8/12; G01S 15/89; G01S 15/8963; G01S 15/8925; G01S 7/5208; G01S 7/52017; G01S 7/52039; G01S 15/8965; G01S 7/52044

See application file for complete search history.

(56) References Cited

U.S. PATENT DOCUMENTS

| | | | |
|---|---|---|---|
| 6,494,841 B1 * | 12/2002 | Thomas ................. | A61B 8/481 600/447 |
| 6,806,623 B2 | 10/2004 | Petersen et al. | |
| 8,622,914 B2 | 1/2014 | Petersen | |
| 2013/0310689 A1 * | 11/2013 | Nishigaki ............ | A61B 8/4483 600/437 |
| 2015/0016227 A1 * | 1/2015 | Brock-Fisher ........ | B06B 1/0292 367/181 |

* cited by examiner

*Primary Examiner* — Sanjay Cattungal (57) ABSTRACT

For phase inversion-based ultrasound imaging with a transmit and receive circuit at an array, a unipolar transmitter is used to reduce the number of high voltage wires. Rather than adding a T/R switch or increasing connections by connecting the receive amplifier to a different electrode than the transmitter, two different receive paths from the element to the receive amplifier are provided. One path is used where the unipolar transmitter ends in one state (e.g., 0V), and the other path is used where the unipolar transmitter ends in another state (e.g., Vtx).

20 Claims, 7 Drawing Sheets

ULTRASOUND TRANSMIT/RECEIVE FOR PULSE INVERSION

BACKGROUND

The present embodiments relate to a transmit and receive circuit for ultrasound imaging. Transmit pulse inversion is used for harmonic and contrast imaging. In a cart-system, transmit pulse inversion is accomplished by using more complex transmitter circuitry and multiple power supplies. For matrix arrays (e.g., 2D array), the transmit and receive circuit may be positioned in the probe with the array rather than in the cart-system. Various problems result from this placement of transmit and receive circuits in the probe housing.

Figure 1:
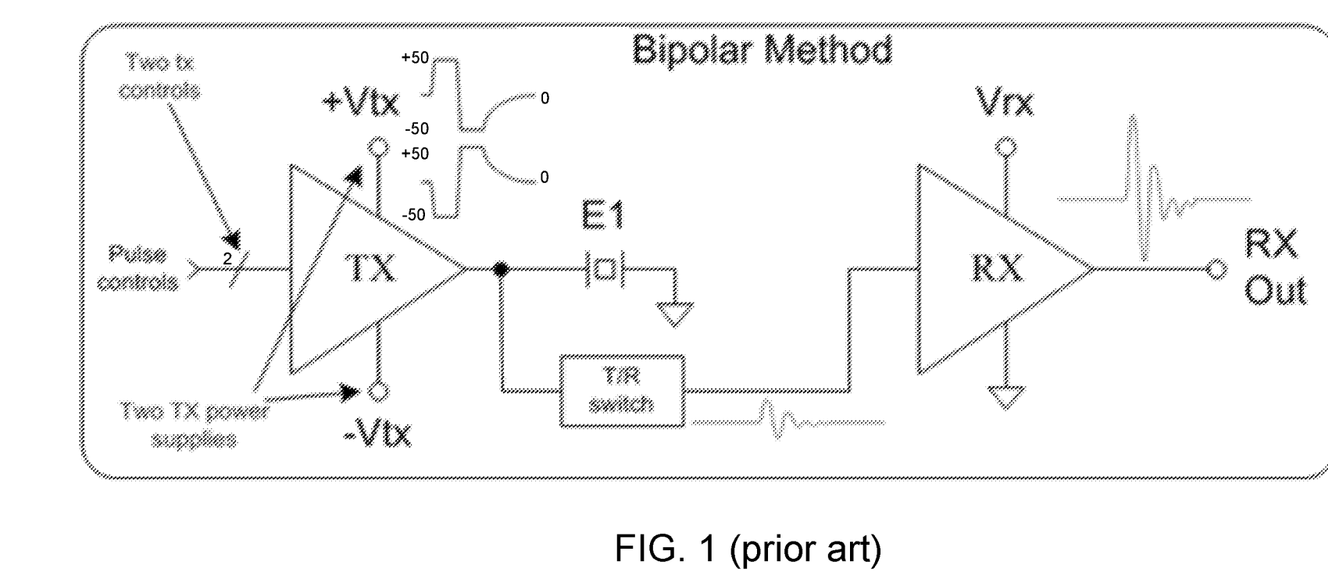
FIGS. 1 and 2 are circuit diagrams of two different prior art transmit and receive circuits.

In one approach shown in FIG. 1, a 2× increase in the complexity of the transmitter circuit and power network is provided. The bipolar transmitter TX uses an explicit Transmit/Receive (T/R) switch to avoid harming the receive amplifier RX by the relatively high voltage (HV) transmitter TX. The T/R switch requires extra HV devices. To operate the bipolar transmitter TX, a double Vtx (+Vtx and −Vtx) power network is used. There may be an extra tracking gate drive supply associated with each TX power supply, so the burden is actually two extra HV wires in the cable connecting to the circuit. HV wires require extra spacing to avoid breakdown, so having two or four HV wires amounts to a significant increase in cabling requirements in addition to twice as many charge storage devices (capacitors) required near the transmit and receive circuit and in addition to dual transmit power supplies elsewhere (e.g., in the transducer pod connector).

Figure 2:
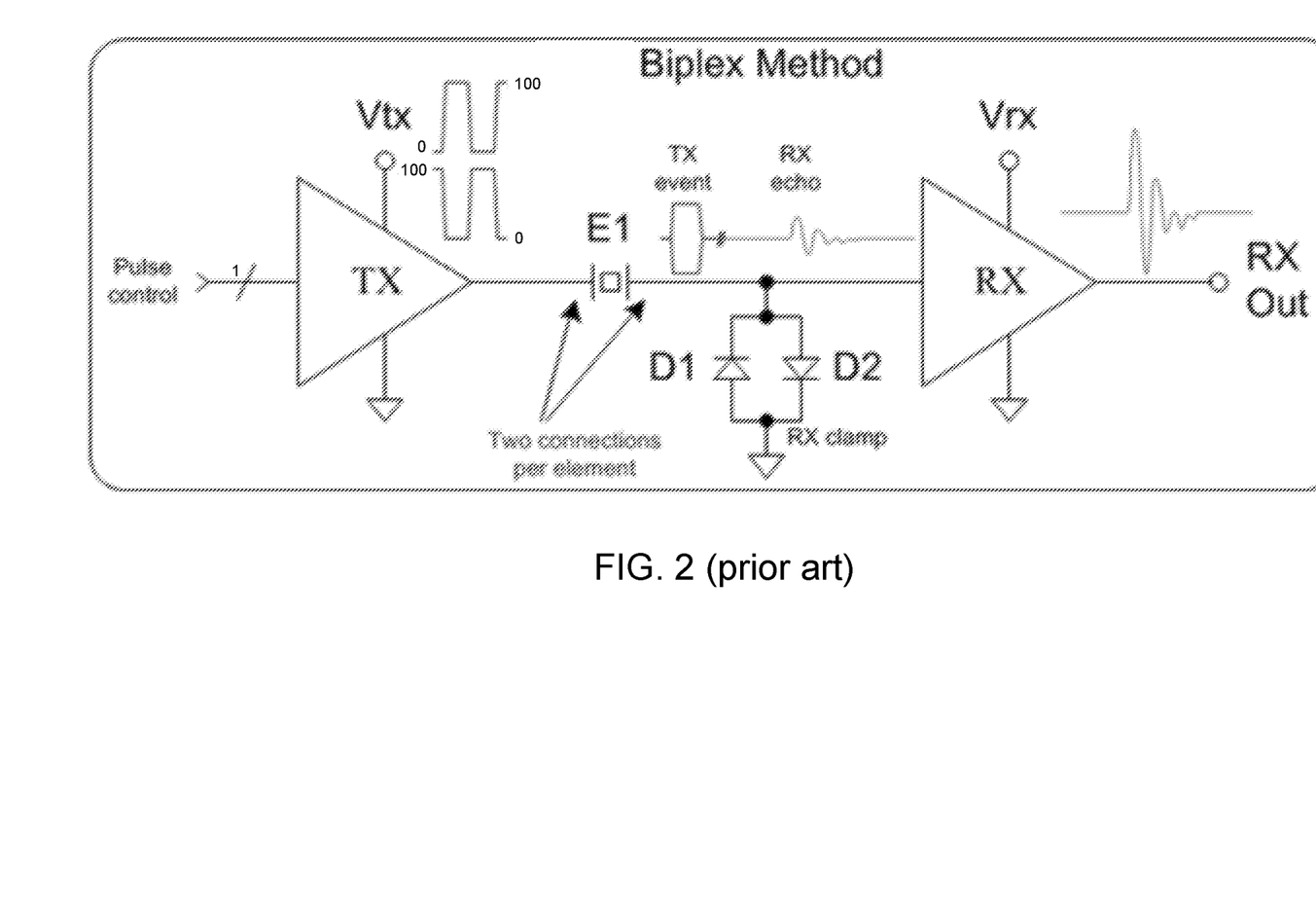

In another approach shown in FIG. 2, a 2× increase in connection to the array is provided. The transmitter TX connects to one electrode of the element E1, and the receive amplifier RX connects to another electrode of the element E1. The two-connections-per-element E1 eliminates the explicit T/R switch and requires only a unipolar transmitter. Doubling the connection count to the array is onerous and difficult where the transmit and receive circuit is in a chip connected directly to the array (i.e., in a chip-on-array solution).

It is a challenge to provide transmit pulse inversion in a matrix transducer (e.g., 2D transducer array) because of tight space and interconnection constraints. Neither approach is acceptable for a matrix intracardiac echocardiography (ICE) catheter with a chip-on-array interconnect where the catheter size benefits from minimization of the number of wires.

SUMMARY

By way of introduction, the preferred embodiments described below include methods, circuits, and systems for ultrasound pulse inversion. A unipolar transmitter is used to reduce the number of HV wires. Rather than adding a T/R switch or increasing connections by connecting the receive amplifier to a different electrode than the transmitter, two different receive paths from the element to the receive amplifier are provided. One path is used where the unipolar transmitter ends in one state (e.g., 0V), and the other path is used where the unipolar transmitter ends in another state (e.g., Vtx).

In a first aspect, a transmit and receive system is provided for ultrasound pulse inversion. A unipolar transmitter connects with an ultrasound transducer element and is configured to generate transmit waveforms ending in a relatively high or low state. A receiver connects with the ultrasound transducer element by first and second separate signal paths from the ultrasound transducer element. A controller is configured to select between the first and second separate signal paths based on the unipolar transmitter ending in the relatively high or low state.

In a second aspect, a transmit and receive circuit is provided for ultrasound. The circuit includes a unipolar transmitter, a receive amplifier, and first and second receive paths connected with an input to the receive amplifier.

In a third aspect, a method is provided for receiving pulse inversion signals in ultrasound. A unipolar pulser generates first and second transmit waveforms in sequence. The first transmit waveform ends with a first voltage state, and the second transmit waveform ends with a second voltage state different than the first voltage state. A first receive signal responsive to the first transmit waveform is routed along a first path from an element to a receive amplifier. A second receive signal responsive to the second transmit waveform is routed along a second path from the element to the receive amplifier. The routing along the first and second paths is selected based on the first and second voltage states.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A transmit and receive (TX/RX) circuit provides transmit pulse inversion from a single transmit power supply. To enable transmit pulse inversion, two of something is needed. FIG. 2 shows two wires per element, and FIG. 1 shows two transmit power supplies. In the current TX/RX circuit, two receive signal paths are used. One of the two paths is selected based on the end-state of a unipolar transmit pulser. Because the required "two of something" is contained within the TX/RX circuit (e.g., within an application specific integrated circuit (ASIC)), there is no increase in interconnect complexity nor a requirement for a more complex transmitter and power network.

The unipolar transmitter end-state problem is solved by providing two alternating current (AC) coupled paths from the element to the receiver. The DC bias in each path is set to the respective transmit waveform end state, allowing use of low voltage devices. The unipolar transmitter may end in either state (high or low), requiring only a single high-voltage power supply. The two separate receive signal paths within the TX/RX circuit extend from the piezoelectric element to a single receive amplifier. Each receive signal path corresponds to one of the two possible transmitter end states. The AC coupling and additional low-voltage switches alternately receive on the two paths when sequentially transmitting alternating polarity transmit waveforms support harmonic and contrast imaging sequences. By ending in alternating states, inverted pairs of waveforms are delivered from a single supply.

The TX/RX circuit may be formed in an application integrated circuit (ASIC), chip, or other circuit arrangement (e.g., discrete components). The TX/RX circuit is used with any transducer and/or ultrasound scanner. In the examples below, the TX/RX circuit is used for a matrix-ICE transducer where the TX/RX circuit is in the catheter by the array, such as a chip-on-array arrangement.

Figure 3:
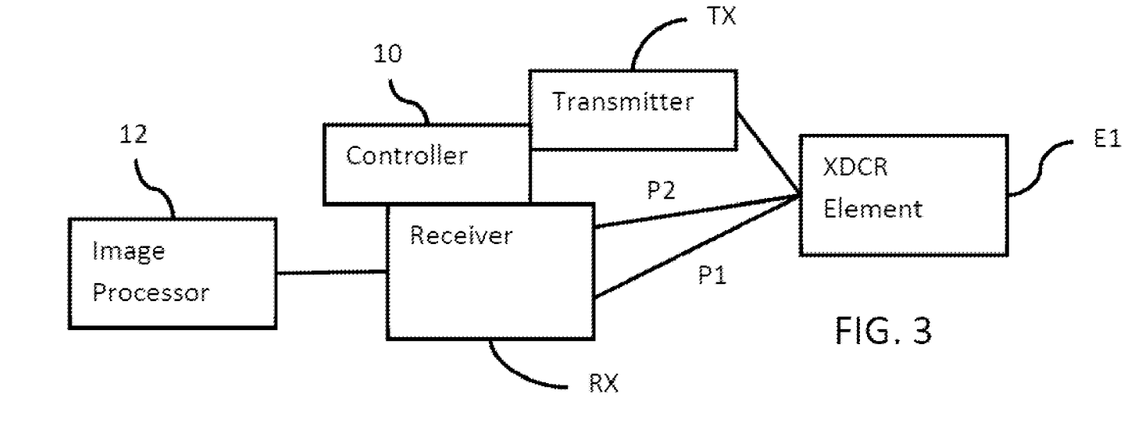
FIG. 3 is a block diagram of one embodiment of a transmit and receive system using dual receive paths.

FIG. 3 shows one embodiment of a transmit and receive system for ultrasound pulse inversion. The transmit and receive system implements the method of FIG. 5. Other methods may be implemented.

The transmit and receive system includes a transmitter TX, a receiver RX, a transducer element E1, a controller 10, two receive paths P1, P2, and an image processor 12. Additional, different or fewer components may be provided. For example, the image processor 12 is not provided. In another example, only the transmitter TX, receive paths P1, P2, and receiver RX are provided (e.g., see FIG. 4 without the element E1).

The transducer element E1 is a piezoelectric, micro-electro-mechanical (i.e., capacitive membrane), or other element to convert between electrical waveforms and acoustic energy. The element E1 is part of an array of such elements, such as a multi-dimensional or matrix array (e.g., 1.5 or 2D distribution of elements in an array). The transmit and receive system includes copies of the same circuit for transmitting and receiving from the different elements. By providing the TX/RX circuit of the system for each of a plurality of channels and corresponding elements E1, phased array scanning may be provided.

Figure 4:
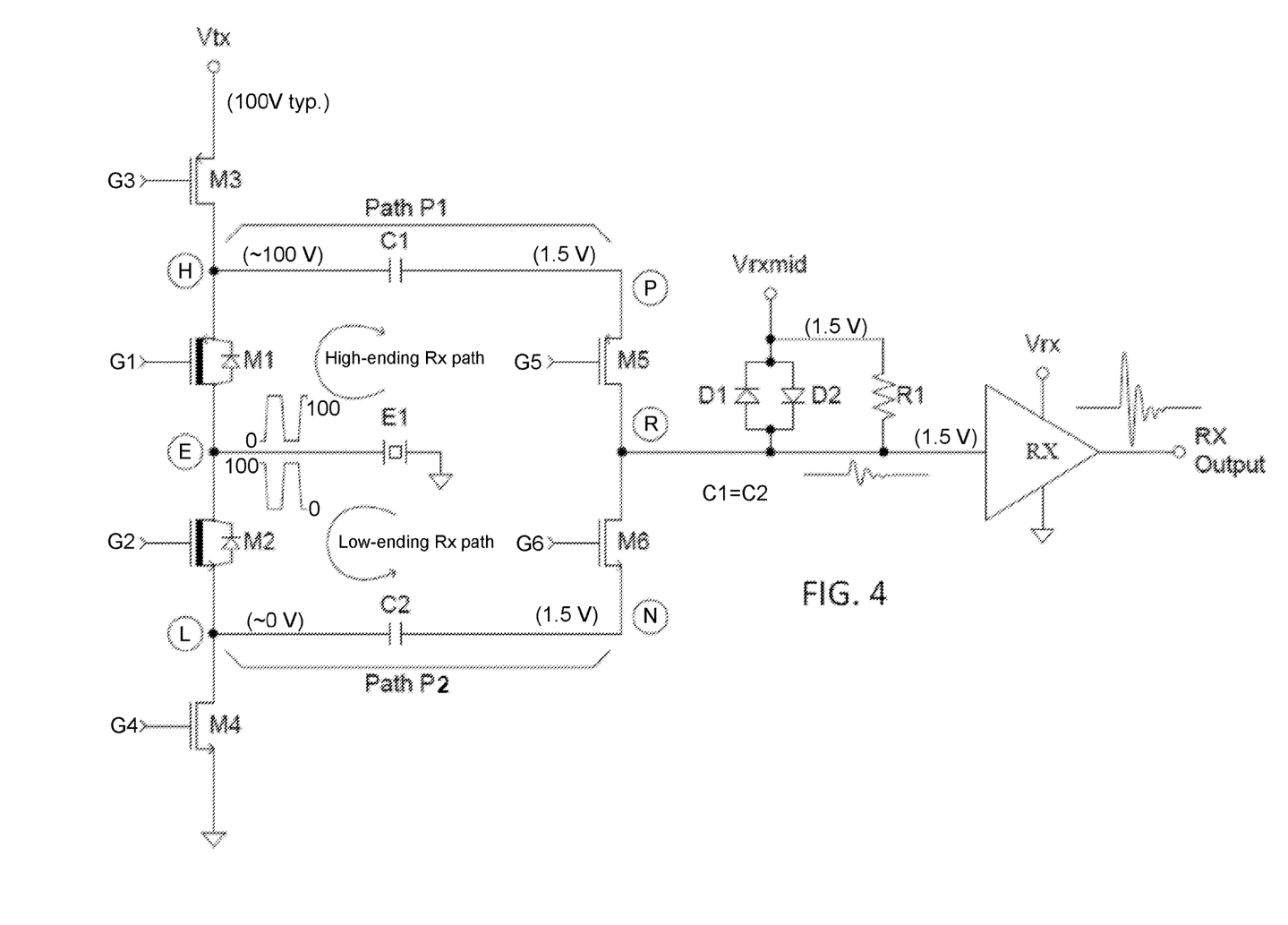
FIG. 4 is a circuit diagram of an example embodiment of a transmit and receive circuit.

The transducer element E1 includes a grounding electrode and a signal electrode. The ground electrode may be part of a grounding plane or sheet covering or common to multiple elements E1. The signal electrode is electrically isolated for each element E1. Both the transmitter TX and the receiver RX connect to the same signal electrode, such as shown in FIG. 1 and FIG. 4. The transmitter TX and the receiver RX connect to the same signal electrode without an intervening T/R switch. The transmitter TX and receiver RX use the dual-path P1, P2 to protect the receiver RX from the high voltage transmit signals of the transmitter TX without a separate T/R switch.

The transmitter TX is a pulser, such as a transistor switch. Any number of transistors may be used. High and/or low voltage transistors may be used. The transmitter TX generates ultrasound pulses. An ultrasound pulse is a pulse at an ultrasound frequency (e.g., 1-10 MHz). A pulse is a single positive or negative pulse. A chain of such pulses may be generated as a waveform. The pulses are unipolar, such as a unipolar square wave. The pulse may not be an exact square wave as the transistors of the transmitter have rise and fall times which are not instantaneous. The transmitter TX is unipolar, so generates sequential waveforms with inverted pulses. One waveform is 180 degrees out of phase with another waveform. A sequence of waveforms with other phase differences may be used.

The receiver RX is a pre-amplifier or receive amplifier. The receiver RX receives signals generated by the element E1 in response to transmission of acoustic energy from the electrical waveforms generated by the transmitter TX. The receiver RX amplifies the receive signals by a fixed or variable amount. For pulse inversion-based scanning, the receiver RX receives different receive signals responsive to the waveforms generated with different relative phasing and/or amplitudes. The receiver RX receives signals responsive to the inverted pulses and amplifies the signals.

The receiver RX connects with the electrode of the element E1 through two different paths P1, P2. Path P1 connects the element E1 to the receiver RX in FIG. 4 via nodes E, H, P and R. Path P2 connects the element E1 to the receiver RX in FIG. 4 via nodes E, L, N, and R. One path P1 is used for receiving signals where the transmitter TX ends with a high voltage in the waveform, and the other path P2 is used for receiving signals where the transmitter TX ends with a low voltage waveform. For pulse inversion, the paths P1, P2 are sequentially used. Separate paths P1, P2 are provided for selection and use based on the phase of the transmit waveforms. AC coupling in the paths allows for protection of the receiver RX from transmit waveforms without a T/R switch.

The controller 10 is a processor, memory, circuit, or other arrangement for controlling the gates of transistors in the transmitter TX and/or receiver RX. The timing of turning on and off the transistors controls operation of the transmitter TX and/or the paths P1, P2. The controller 10 causes generation of the transmit waveforms in sequence with phase inversion and receipt of responsive signals in sequence through the different paths P1, P2.

The image processor 12 is an ultrasound beamformer, detector, filter, or another processor. The image processor 12 includes an analog-to-digital converter to convert the receive signals to digital form. Alternatively, the receive signals are processed in analog format. The image processor 12 filters, calibrates, or adjusts received signals to account for any mismatch of the paths P1, P2. Signals for one path P1 may be amplified or reduced in amplitude relative to the signals of the other path P2 to account for mismatch. Mismatching in frequency response may be accounted for by adjustment of the signals. For example, the two receive paths may be independently equalized digitally. In alternative embodiments, accounting for mismatch is not performed.

The transmit and receive system is part of an ultrasound system. A coaxial cable connects the element E1 with an ultrasound scanner. The receiver RX is part of the receive beamformer or a separate component. The transmitter TX is part of the transmit beamformer. The transmit beamformer generates waveforms for different elements. The waveforms are converted to acoustic energy by the elements E1. Acoustic echoes responsive to the transmitted acoustic energy are received by the elements E1 and converted to the receive signals. The amplified receive signals output by the receiver RX are receive beamformed across the array.

The transmitter TX, receiver RX, controller 10, and/or image processor 12 are within a transducer probe or spaced from the probe by coaxial cables or other types of transmission lines. For example, the transmitter TX, controller 10, and receiver RX are in the transducer probe, such as in an integrated circuit chip mounted against an array. Transmitters TX and the controller 10 form the transmit beamformer. The image processor and receive beamformer are separated from the transducer probe by coaxial cables, which carry the high voltage supply and receive signal lines. Other arrangements may be used, such as the element E1 being in the probe and the remainder of the transmit and receive system being in a transducer connector or ultrasound scanner separated from the transducer probe by coaxial cables.

In one embodiment, the integrated circuit with the transmitter TX and receiver RX is positioned within a transducer housing for connection to a multi-dimensional array, such as an array of an ICE catheter. By integrating both high and low voltage switches in the same integrated circuit, a small transmit beamformer for use in a probe is provided. The same semiconductor substrate is used for both the high voltage and low voltage switches. Multiple transmitters TX and receivers RX, such as 64, 128, 256, or other number (e.g., over 1000 for a matrix or 2D array), may be integrated into the same chip or application specific integrated circuit. The integrated circuit is small enough to fit under or within the shadow of the array, so may be mounted in the ICE catheter with the array. In one matrix ICE catheter example, 1728 or 2304 elements and corresponding transmitters TX and receivers RX are used. All the transmitters TX and receivers RX are on a single integrated circuit.

FIG. 4 shows one example embodiment of the transmitter TX and receiver RX. The transmitter TX and receiver RX are integrated into a TX/RX circuit for ultrasound. This arrangement puts the "two of something" detail inside a circuit, such as in an ASIC. This integration avoids extra external wiring complexity and results in a compact and simple solution for use with pulse inversion in ultrasound imaging.

Additional, different, or fewer components may be provided. Additional biasing (e.g., resistors), clamping (e.g., diodes), or switches (e.g., transistors) may be added at nodes H, P, L, or M to better manage DC operating points during and after the transmit event to compensate for parasitic effects or non-ideal device characteristics.

The controller 10 is not shown in the TX/RX circuit. The controller 10 is part of the TX/RX circuit. For example, the controller 10 includes transistors and memory for receiving a control signal and causing operation of the transmitter TX and receiver RX based on the control signal. The transistors and memory of the controller 10 are in a same ASIC with the TX/RX circuit. Alternatively, the controller 10 or parts of the controller 10 are in a separate component, chip, or integrated circuit.

The TX/RX circuit is integrated in a same chip. For example, an ASIC includes one or more of the TX/RX circuits without the element E1 shown in FIG. 4. The different components are formed using the same or different processes on the same semiconductor substrate, such as using CMOS processes.

The circuit, ASIC and/or the chip may have various inputs and outputs. For example, a trace and pad are provided to receive power from a positive or negative voltage source, Vtx. This power source input is a pad or connector for connection with the power source. The voltage provided at the power source is supplied by a voltage rail, such as a fixed or variable voltage source. Other voltage regulators may be provided, such as providing for a voltage supply or regulation integrated within the integrated circuit. Any voltage may be provided, such as +/−10-200 volts (e.g., +100 V shown in FIG. 4) for pulse wave operation or 1-20 volts for continuous wave operation. Since a unipolar transmitter TX is used, only one power source connector is used. Any other voltage levels for the circuit, such as a tracking supply, may be generated by a voltage divider or voltage regulator in the circuit. Alternatively, addition power source inputs are provided for voltages at different levels. Both negative and positive powers may be avoided since the transmitter TX is unipolar. Alternatively, a bipolar transmitter is used so both positive and negative powers and corresponding power source inputs are provided.

The power from the power source input is used to generate waveforms. Power derived from the power source input or from other sources may be used for the controller 10 and/or for DC bias. For example, gate voltages may be only 3-4 volts different than a bias level or ground. This voltage difference is selected to avoid exceeding the gate oxide breakdown voltage of the low voltage switches.

Another connector is a ground connector. The ground is shared with the element E1 and/or the ultrasound scanner.

Yet another connector is a transducer element connector. The interconnect of the circuit with the element E1 is formed by compression bonding a pad of the circuit with the electrode of the element E1 or to the element E1 where the pad is the electrode. Other interconnections may be used, such as solder bump, jumper, flexible circuit, or flip-chip connections.

A logic power supply connector, safety override control connectors, pulse control connectors, or other connectors may be provided on the circuit or chip. Additional, different or fewer inputs and outputs may be provided.

The connections of the TX/RX circuit provide for one interconnect for each element E1. The connection of the transmitter TX and receiver RX to the same electrode allows for a minimal number of interconnects with the array. This may be particularly advantageous for a matrix array (e.g., multi-dimensional distribution of elements) where interconnection space is limited. The unipolar transmitter TX allows for a minimal number of high voltage lines in a transducer cable, such as a single high voltage line and a ground conductor (e.g., shield). Avoiding the T/R switch uses less circuit space and requires fewer high-voltage transistors. In combination, a chip-on-array arrangement may be provided for a matrix array for ICE where the TX/RX circuit fits within the element shadow (i.e., area on of TX/RX circuit in the ASIC is the same or less than area of an element E1 and/or area of ASIC is the same or less than an area of the array). In other applications where space is not at such a premium, multiple chips may be used in a "slice" (e.g., one chip for each of sub-set groupings of elements) approach to reduce the number of channels per chip or to provide more functionality.

The transmitter TX is shown as four switches M1-4 in FIG. 4. The TX/RX circuit includes high voltage switches M1, M2, low voltage switch arrays M3, M4, and/or other components. The diodes shown across M1 and M2 are part of the high-voltage FETs forming the high voltage switches M1, M2. One high voltage transistor and one low voltage transistor connect in series between the transducer element connector (e.g., node E) and the power source input (e.g., Vtx). The other high voltage transistor and the other low voltage transistor connect in series between the transducer element connector (e.g., node E) and the ground connector (e.g., ground). The one high voltage switch M1 connects through the one low voltage switch M3 to a power supply, and the other high voltage switch M2 connects through the other low voltage switch M4 to ground.

In one embodiment, the low-voltage switches M3, M4 are low voltage transistors, such as 3.3V field effect transistors (FETs). The low voltage transistor may be manufactured using CMOS processes. The low voltage switches M3, M4 may be of a same type or different type of switches from each other. The direction of the arrow indicates the polarity.

An arrow pointing inward is a P-channel FET. An arrow pointing outward is N-channel FET. The low voltage switches M3 and M4 are of the opposite polarity, and the low voltage switches M5 and M6 are of the same or different polarity as each other. Each low voltage switch M3, M4 has a turn-on threshold of less than 6 volts, such as a 1 to 2-volt threshold. Greater or lesser threshold voltages may be provided. The low voltage switches M3, M4 have a thinner oxide layer at the gate or other differences in dimensions for operation with exposure to a lesser voltage than the high voltage switches M1, M2. In one embodiment, the low voltage switches M3, M4 are smaller than the high voltage switches M1, M2. For example, the low voltage switches M3, M4 are operable with voltage supplies or differences across the gate and source less than 10 volts, such as voltages of 2.5 to 12 volts. The drain-to-source resistance of the low voltage switches M3, M4 is much lower, such as ten times smaller, than the drain to source resistance of the high voltage switches M1, M2. For example, the resistance of the low voltage switches M3, M4 is 50 ohms or less. Lesser resistance is provided by having a thinner oxide and a shorter channel. Greater resistances may be provided with a similar or different ratio of resistances from the high voltage switches M1, M2 to the low voltage switches M3, M4.

The high-voltage switches M1, M2 are high-voltage FETs (a non-CMOS device). The high voltage switches M1, M2 form a waveform generator and are complimentary field effect transistors, but may include other types of transistors or switches. Each of the high voltage switches M1, M2 may be of a same or different type of switch or transistor. FIG. 4 shows the high voltage switches M1, M2 as opposite polarity. The high voltage switches M1, M2 are operable with at least 10 or more volts, such as allowing for a 10 to 200-volt supply at the input power connector. For example, each of the high voltage switches M1, M2 is sized to have a gate oxide and other associated dimensions for operating with a 10 or 200-volt power supply. The drain-to-source resistance in the "on" state may be of any of various values, such as being 500 or less ohms. The high voltage switches M1, M2 are integrated on a same chip or within a same circuit.

Gate oxide thickness determines the voltage limit on gate-to-source breakdown voltage. The source is indicated by the polarity arrow. Other dimensions determine the drain-to-source breakdown voltage. Some high-voltage transistors have the same gate oxide thickness as the CMOS devices, but the drain dimensions are modified to increase the drain-source breakdown. In other embodiments, the high voltage transistors have a thicker gate oxide than the CMOS but mainly because the CMOS is very low voltage. In one embodiment, a 1.8V CMOS process with 3V HV FET oxide is used for the high voltage switches M1, M2, so the oxides are different.

The high-voltage switches each have a gate, source, and drain. The sources are connected with the drains of the low-voltage switches M3, M4. The gate connects with the gate voltage output of the controller 10. The drain connects with the output to the element E1, represented as node E. Other connections, such as with or without intervening components, may be used.

The high-voltage switches M1, M2 are configured to generate a transmit pulse and corresponding waveform. This operation may occur in one of two ways. In one approach, a relatively constant voltage at the gate of switches M1, M2 is applied during transmit operations. The voltage at the gate is constant during the on/off operation of the high-voltage switches M1, M2. The difference in the gate and source voltages activates or not the high-voltage switches M1, M2.

The low-voltage switches M3, M4 may be used to create or not a sufficient difference between the source voltage and the gate voltage, such as being no difference for "off" and being at least 1, 2, 3, or greater volts difference for "on." In the embodiment of FIG. 4, the gate voltages are 97 volts for switch M1 and 3 volts for switch M2 and voltages at the sources (nodes H and L) are 100 volts and 0 volts, respectively, when switches M3, M4 are closed. Other absolute voltages and/or difference in voltages may be used. The voltage difference is greater than the threshold-on voltage of the high-voltage switches M1, M2. In one embodiment, the high-voltage switches M1, M2 turn on and off only by the low-voltage switches M3, M4 connected in cascode turning on and off. By operating switches M3, M4 to turn on and off sequentially in opposition to each other (M3 on when M4 off and vice versa), the positive voltage or the ground of nodes H and L are connected by the high voltage switches M1, M2 to the element E1 through node E, generating a unipolar waveform.

In another approach, the gates of the high-voltage switches M1, M2 are sequentially turned on and off in opposition. The low voltage switches M3, M4 are always on during transmit or turn on and off when the voltage or the ground of nodes H and L are connected by the high voltage switches M1, M2 to the element E1 through node E, generating a unipolar waveform. Other pulser arrangements and/or approaches may be used, such as a single switch to connect either high voltage or ground with the output node E.

In either approach, the high voltage switches M1, M2 are operable to generate a transmit pulse on the output node E. The high voltage switch or switches M1, M2 form a switching pulser. More complex pulsers may be provided using a greater number of switches. The high voltage switches M1, M2 generate transmit pulses. By turning on, then off, a pulse is generated. By turning on, then off repetitively, a pulse train forming the waveform is generated. Either a single pulse or multiple pulse train type of waveform may be used.

The pulse inversion transmit waveforms are generated with a unipolar transmitter TX, which connects to the single power supply Vtx for switching between ground and the voltage of the power supply. The switches M1-4 of the unipolar transmitter TX operate to generate transmit waveforms with different (e.g., opposite phases) in sequence. FIG. 4 shows two such waveforms each being 1.5 cycles, but opposite phases. One waveform starts at 0 volts, includes a single 100-volt pulse returning back to 0 volts, and then transitions up to 100 volts, ending at 100 volts. The other waveform starts at 100 volts, includes a single 0-volt pulse returning back to 100 volts, and then transitions back to 0 volts, ending at 0 volts. With this arrangement, the waveforms with opposite phase may be generated in sequence since the ending voltage state due to the ½ cycle of one waveform is the beginning voltage state of the next. For pulse inversion, the transmit waveforms end in a relatively high or low state, 0 or 100 volts in this example.

The receiver RX connects to the element E1 through the two paths P1 and P2. These are two separate signal paths P1, P2. The paths P1, P2 are part of or separate from the receiver RX, but are included in the circuit, such as in the ASIC or chip forming the integrated circuit. The paths P1, P2 connect the input (e.g., node R) of the receive amplifier with the element E1 through the element connector (e.g., node E).

The input to the receiver RX may be clamped. The diodes D1, D2 and resistor R1 connect the input node R to a mid-level voltage source Vrxmid. The mid-level voltage source is any voltage, such as 1.5V. In the example of FIG.

4, the receiver RX operates with a 3-volt power, Vrx. This arrangement passively protects the receiver RX.

Each path P1, P2 includes a capacitor C1, C2, and low voltage switches M5, M6. Additional, different, or fewer components may be included. For example, the high voltage switches M1, M2 are included in the path. The high voltage switches M1, M2 are shared between the paths P1, P2 and the transmitter TX. One receive path P1 connects between one high voltage switch M1 and one low voltage switch M3, and the other receive path P2 connects between the other high voltage switch M2 and the other low voltage switch M4.

The capacitors C1, C2 are alternating current (AC) coupled in the paths P1, P2. The capacitor C1 couples the high voltage node H (e.g., about 97 volts) to the low voltage node P, so is a high voltage capacitor. The capacitor C2 couples the low voltage node L (e.g., about 3 volts) to the low voltage node N, so may be a low voltage capacitor. For matching the two paths P1, P2, both capacitors C1, C2 may be matched or identical high voltage capacitors (e.g., C1=C2). In one embodiment, $1/(2\pi R1C1) \approx 500$ kHz, but other arrangements may be used. Alternatively, capacitor C1 is high voltage, and capacitor C2 is low voltage, so are not identical but are matched to the extent possible.

The switches M5, M6 of the paths P1, P2 are low voltage switches, such as the same or different type of low voltage transistors as the switches M3, M4. The low voltage switches M5, M6 connect in series with the capacitors C1, C2, respectively, along the paths P1, P2, respectively. The AC coupling of the capacitors C1, C2 allows for the switches M5, M6 to be low voltage transistors, so the switches M5, M6 connect between the capacitors C1, C2 and the input (e.g., node R) of the receiver RX.

Other TX/RX circuits may be used, such as circuits where the paths P1, P2 do not share the high voltage switches M1, M2 with the transmitter TX.

The controller 10 drives the switches M1-6 with gate signals G1-6. The gate signals G1-6 are controlled for transmit and receive operations.

For transmit operation, the switches M5, M6 of the receive paths P1, P2 are open. The switches M1-4 of the transmitter are driven to operate in either of the approaches discussed above.

For receive operation, the controller 10 is configured by hardware, software, and/or firmware to select between the separate signal paths P1, P2 based on the unipolar transmitter TX ending in the relatively high or low state. In the example of FIG. 4, the path P1 is used where the transmitter TX ends on the higher voltage (e.g., 97 volts or about 100 volts), and the path P2 is used where the transmitter TX ends on the lower voltage (3 volts or about 0 volts). The switches M1, M2, the switches M5, M6, or both are used to select. The gates G1, G2, G5, and/or G6 are controlled to select the path.

In one embodiment, where the unipolar transmitter TX ended in the relatively high state, the high voltage switch M1 is closed, the high voltage switch M2 is open, the low voltage switch M5 is closed, and the low voltage switch M6 is open. This configuration of open and closing forms the path P1 for receiving signals and closes or breaks the path P2. Where the unipolar transmitter TX ended in the relatively low state, the high voltage switch M2 is closed, the high voltage switch M1 is open, the low voltage switch M5 is open, and the low voltage switch M6 is closed. Regardless of the end state, at least one of the switches M3, M4 are opened during receive operation. This configuration of open and closing forms the path P2 for receiving signals and closes the path P1.

After each transmit operation (i.e., generation of a transmit waveform of one or more cycles or pulses), one of the receive paths P1, P2 is selected. The selection is based on the ending state of the transmitter TX (i.e., whether the higher or lower voltage is the last part or state of the waveform). The different paths P1, P2 are used sequentially. Transmit waveforms that end in the high state leave the element E1 connected to node H by leaving high voltage switch M1 closed while high voltage switch M2 is left open. Low voltage switches M3 and M4 are both closed during transmit but are both opened during receive. In the cascode arrangement where high voltage switches M1 and M2 have constant gate bias and their conducting state is controlled by the low voltage switches M3 and M4, both the low voltage switches M3 and M4 are opened during receive. In other transmitter arrangements, the low voltage switches M3 and M4 may alter during receive based on the path P1, P2 being used or one may be open and the other closed at different times.

With element E1 connected to node H via high voltage switch M1, capacitor C1 AC couples the receive signal to node P and then to node R via closed low voltage switch M5. Low voltage switch M6 is left open during this high-ending transmit and receive event. Node R is direct current (DC) biased to an appropriate level for the receive amplifier RX to operate. Large signals at node R are clamped by the pair of anti-parallel signal diodes, D1, D2. A complimentary sequence is used for transmit waveforms that end in the low state culminating in the receive path P2 from element E1 to node L via closed high voltage switch M2 and from there through capacitor C2 and low voltage switch M6 to node R.

The different paths P1, P2 are DC biased to provide receive signals at a same voltage to the receive RX. One path P1 receives the signals at the higher voltage based on the higher end state of the transmit waveform. The AC coupling causes this higher voltage to be shifted to the DC level of the receiver RX. The other path P2 receives the signals at the lower voltage based on the lower voltage end state of the transmit waveform. The AC coupling causes this higher voltage to be shifted to the DC level of the receiver RX. By having the two different paths, the unipolar transmitter RX with only one high voltage power source and connection may be used without a T/R switch even though the transmitter TX and receiver RX share a same connection to the element E1 (i.e., connected to same electrode of the element E1). This results in fewer high voltage lines to the transducer array, a minimum number of interconnections, and smaller chip real-estate requirements due to fewer high voltage switches.

The AC coupling may not be matched. As a result, the signals input to the receiver RX through one path P1 may be different in amplitude and/or frequency response than the signals input to the receiver RX through the other path P2. In one embodiment, a filter, extra amplifier, or other circuit is added to one of the paths P1, P2 to normalize or match. In another embodiment, the capacitors C1, C2 are better matched. In yet another embodiment, digital signal processing is used to normalize or match the signals. An image processor after the receiver RX is configured to compensate for mismatch between the AC-coupled capacitors in signals output from the receiver RX. Signals from the one path P1 are processed differently than the signals from the other path P2 before combining, such as before combining in a receive beamformer for isolating information at a harmonic band.

Figure 5:
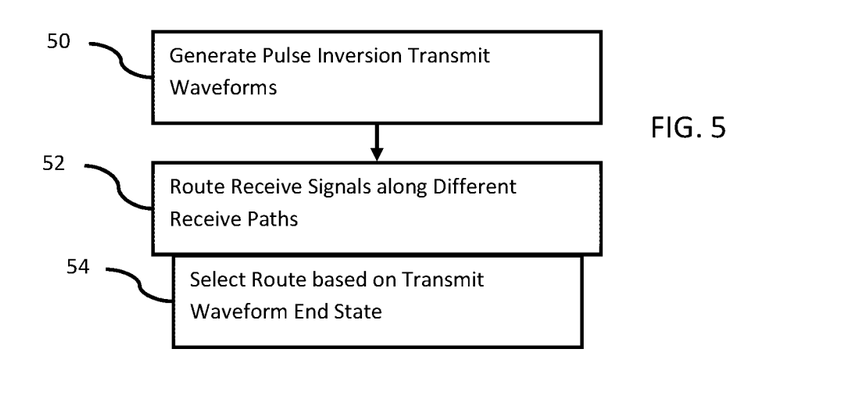
FIG. 5 is a flowchart diagram of one embodiment of a method for receiving pulse inversion signals.

FIG. 5 shows one embodiment of a method for receiving pulse inversion signals in ultrasound. A sequence of two or more waveforms is generated. In response to each waveform, receive signals are received and amplified. The receive operations are interleaved with the waveform generation. With pulse inversion, the transmit waveforms have different phases. The receive signals are routed along different paths to the receive amplifier based on the phase of the transmit waveform.

The method uses the system of FIG. 3, the TX/RX circuit of FIG. 4, or another integrated circuit, chip, or TX/RX circuit. The switches of the transmitter are shared or not shared for receive routing along different paths. The method uses two different receive paths to route signals from the element to a receive amplifier, receiver, or another common path (e.g., channel of a receive beamformer). Additional paths may be provided, such as where more than two end states are possible (e.g., relative phasing other than inversion).

Additional, different, or fewer acts than shown in FIG. 4 may be provided. For example, an act for relative processing of received signals to account for mismatching in the different paths is provided.

The acts are performed in the order shown (e.g., numerical or top-to-bottom). Since the transmit and receive operations are interleaved, acts 50-54 are interleaved. One waveform is generated in act 50, and one of the paths is selected in act 54 for routing the signals in act 52. The acts are then repeated for the next transmit waveform. Other orders may be provided.

In act 50, a pulser or other waveform generator generates transmit waveforms in sequence. The transmit waveform sequence includes periods in between each pair of transmit waveforms for receiving, providing transmit, receive, transmit, receive, and so on. Each transmit waveform has any number of cycles, such as 1.5-5 cycles, and corresponding pulses.

The different transmit waveforms have different phases. For pulse inversion, each waveform is 180 degrees out of phase with the previous waveform. Other relative phases may be used, such as using three different relative phases. Due to the different phasing, different transmit waveforms have different ending voltage levels. For pulse inversion with a unipolar waveform, the ending state of the waveforms are at maximum amplitude or minimum amplitude. For example, one waveform ends at about the supply voltage level (e.g., +/−100 volts) and another waveform ends at about ground (e.g., 0 volts). About is used to account for voltage loss due to transistor or other pulser operation (e.g., parasitic or non-ideal device behavior).

In one embodiment, the transmit waveforms are generated by a unipolar pulser or waveform generator. For unipolar waveforms, one high-voltage transistor is cycled on and then off for each pulse. Two switches may be used in a unipolar transmitter, one to pull up and the other down (to zero). Cascode or trimming may be used, such as using low voltage switches connected to the source of high voltage switches to turn on and off the high voltage switches where the gate voltage for the high voltage switches is constant. Alternatively, the gates of the high voltage switches may be controlled to generate the waveform. Other arrangements for unipolar pulsers may be used. In alternative embodiments, a bipolar pulser is used. For example, one high-voltage transistor as trimmed by a low-voltage transistor is cycled on and then off for each positive pulse. Another high-voltage transistor as trimmed by a low-voltage transistor is cycled on and then off for each negative pulse. More than one high-voltage transistor may be used for generating the positive pulse and/or negative pulse for bipolar and/or unipolar waveform generation. Additional paths may be added to account for additional end states.

The ultrasound pulses are output from a transducer in response to application of the generated waveform to the transducer. The same transmitter and associated waveform generator may be used for generating either pulsed waves or continuous waves with different phases in ultrasound imaging. For harmonic and contrast agent imaging modes, multiple waveforms may be generated, but 180 degrees out of phase.

In response to the transmitted ultrasound energy, acoustic echoes are received by the transducer. Each element converts the receive echoes into an electrical signal. The electrical signal is amplified by a receive amplifier and then used for beamforming with received electrical signals from other elements. For harmonic or contrast agent imaging, the receive signals responsive to transmit waveforms with different phases may be summed. By summing the received signals, the harmonic or other response of the tissue or contrast agent is provided. Subtraction or other operations to combine the received signals may be used. The summed receive signals are then receive beamformed.

In act 52, the controller routes receive signals during receive operation. The routing is along one of two or more different paths. Multiple paths from the element to the receive amplifier are provided. The receive signals are routed along one of the multiple paths. Different receive signals may be routed along different paths. Receive signals responsive to one transmit waveform are routed along one path, and receive signals responsive to a different transmit waveform are routed along a different path. For pulse inversion, the routing may be repeated.

The different paths include at least one different component. For example, a different capacitor and/or transistor is provided in each path. In one embodiment, each path is formed from a high voltage transistor of the transmitter, an AC coupling capacitor, and a low voltage transistor. Different paths use different high voltage transistors, capacitors, and low voltage transistors. The transistors are used to route, such as opening or closing, forming the path from the element to the receive amplifier. In other embodiments, the two paths include two receive amplifiers operating alternately with their outputs multiplexed, replacing the high voltage capacitors in the paths with high voltage capacitors at the output of the multiplexor. Power to the receive amplifiers would also be multiplexed to save power on the amplifier not being used.

The different paths have different DC bias levels. The AC coupling capacitors provide a transition from the DC bias level to a voltage level for the receive amplifier. The capacitors serve to shift the DC level while preserving the AC signal. Transistors (e.g., level shifters) may be used instead of the capacitors.

The different paths are used for different phasing. The transmit waveforms have different relative phasing. In act 54, the controller selects the route for the receive signals based on the phasing of the transmit waveforms. The phasing difference is reflected in the end state or voltage of the transmit waveform. The waveforms end at different voltages. For unipolar, the transmit waveforms end at one of two states, such as relatively high magnitude and relatively low magnitude (e.g., +/−100 volts and 0 volts). The controller selects the route based on the ending state. For receiving signals responsive to a transmit waveform ending with relatively high magnitude, one route is selected. For receiving signals responsive to a transmit waveform ending with a relatively low magnitude, another route is selected.

In the TX/RX circuit of FIG. 4, the high voltage switch M1 is closed to end with the transmit waveform in the high state. The high voltage switch M1 remains closed to select the path P1 for receiving responsive receive signals. The high voltage switch M2 is open to end with the transmit waveform in the high state. The high voltage switch M2 remains open to deselect the path P2 for receiving the responsive receive signals. Conversely, the high voltage switch M1 is open to end with the transmit waveform in the low state. The high voltage switch M1 remains open to deselect the path P1 for receiving responsive receive signals. The high voltage switch M2 is closed to end with the transmit waveform in the low state. The high voltage switch M2 remains closed to select the path P2 for receiving the responsive receive signals.

Figure 6:
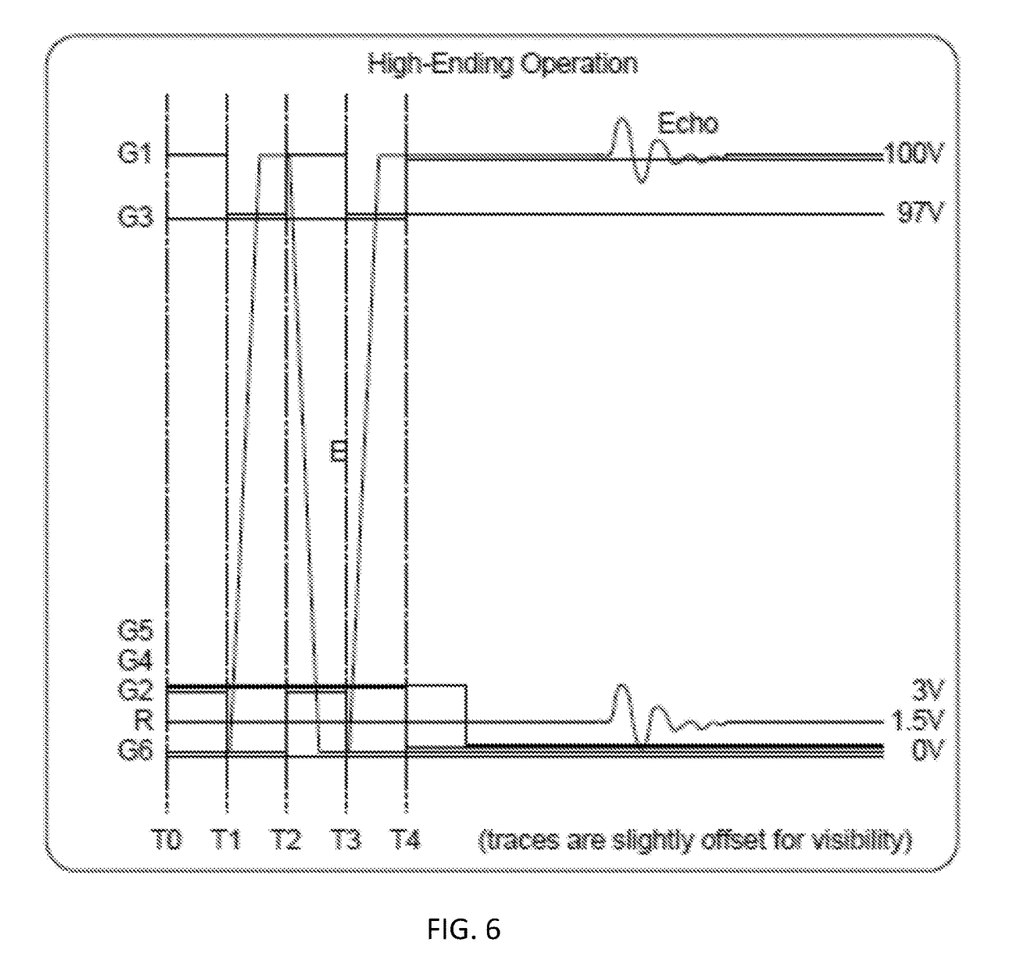
FIG. 6 illustrates a drive gate control sequence for a unipolar transmitter ending in a high state.
Figure 7:
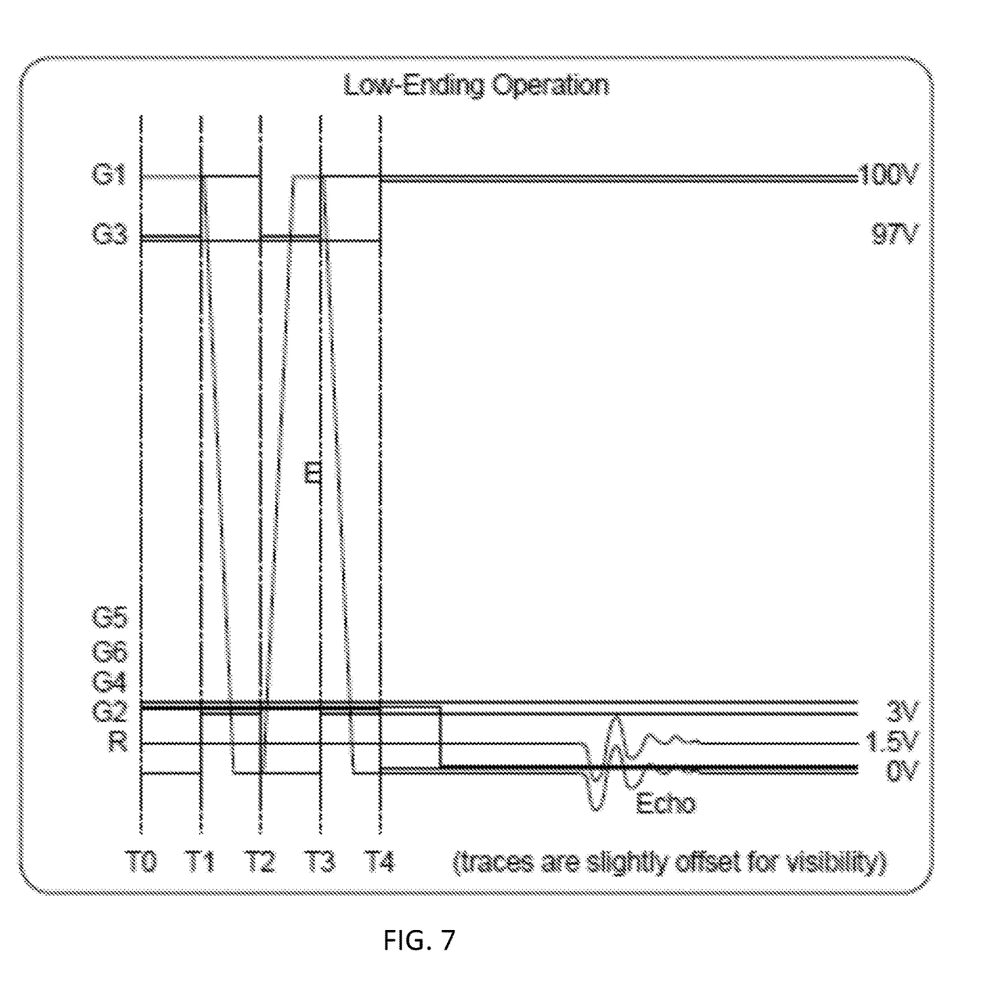
FIG. 7 illustrates a drive gate control sequence for a unipolar transmitter ending in a low state.

FIGS. 6 and 7 show example gate control signals for routing and selecting using the TX/RX circuit of FIG. 4. The traces shown in FIGS. 6 and 7 are slightly offset for visibility, but overlap in actual use. The gate control signals represent a code used to operate the TX/RX circuit. The code is stored in the chip or off the chip. In one embodiment, the code is stored in the chip after manufacture and measurement or calibration. The storage may be a fused-ROM or other type of memory. The code may be stored for use, or read out, interpolated and provided back to the chip.

FIGS. 6 and 7 show the low voltage as 0 volts and the high voltage as 100 volts. Based on the DC bias for the different paths, 97-volt and 3-volt tracking or following voltages are used for gate control. The input to the receive amplifier is shown as R, DC biased to 1.5 volts.

The gate control signals for G1 and G3 operate with a high DC bias. The gate control signals for the remaining switches operate with a low DC bias. The times T0-T4 correspond to transmit operation where unipolar waveforms are generated. FIG. 6 shows starting with the waveform E at a low voltage and ending at a high voltage, and FIG. 7 shows starting with the waveform E at a high voltage and ending at a low voltage. In both cases for this example, G3 and G4 are on at all times T0-T4. G1 and G2 cycle on and off to generate the waveform E. G5 and G6 are off at all times T0-T4.

After the transmit waveform is generated, the control signals are set to route the receive signals (Echo) along a selected path. The control signals are constant during the receive operation. For the high-ending operation of FIG. 6, G2, G3, G4, and G6 are off. G1 and G5 are on. The receive signals ride on the 100-volt potential and connect from node E to node H via switch M1 once switch M3 opens. From node H, the receive signal (Echo) is AC coupled via capacitor C1 to node P and then connected via switch M5 to node R. For the low-ending operation of FIG. 7, G1, G3, G4, and G5 are off. G2 and G6 are on. The receive signals ride on the 0-volt potential and connect from node E to node L via switch M2 once switch M4 opens. From node L, the receive signal (Echo) is AC coupled via capacitor C2 to node N and then connected via switch M6 to node R.

Other control circuitry, control signals, transmitter components, or arrangements may be used. More than two different paths may be used for routing, such as where three different ending voltage levels are provided. Different combinations of components may be used on the same chip, spread between multiple chips, or provided as a circuit not integrated on a chip.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A transmit and receive system for ultrasound pulse inversion, the transmit and receive circuit comprising:
   an ultrasound transducer element;
   a unipolar transmitter connected with the ultrasound transducer element, the unipolar transmitter configured to generate transmit waveforms ending in a relatively high or low state;
   a receiver connected with the ultrasound transducer element by first and second separate signal paths from the ultrasound transducer element; and
   a controller configured to select between the first and second separate signal paths based on the unipolar transmitter ending in the relatively high or low state.

2. The transmit and receive system of claim 1 wherein the unipolar transmitter, receiver, and controller are in an application specific integrated circuit.

3. The transmit and receive system of claim 1 wherein the ultrasound transducer element comprises a grounding electrode and a signal electrode, and wherein the unipolar transmitter and the receiver both connect to the signal electrode.

4. The transmit and receive system of claim 3 wherein the unipolar transmitter and the receiver both connect to the signal electrode without an intervening transmit/receive switch.

5. The transmit and receive system of claim 1 wherein the ultrasound transducer element is part of a multi-dimensional transducer array in an intracardiac echocardiography catheter, the unipolar transmitter and the receiver being in the intracardiac echocardiography catheter.

6. The transmit and receive system of claim 1 wherein the unipolar transmitter has a single high-voltage power supply.

7. The transmit and receive system of claim 1 wherein the unipolar transmitter comprises first and second high voltage switches, the first high voltage switch connected through a first low voltage switch to a power supply, the first signal path connected between the first high voltage switch and the first low voltage switch, the second high voltage switch connected through a second low voltage switch to ground, the second signal path connected between the second high voltage switch and the second low voltage switch.

8. The transmit and receive system of claim 7 wherein the controller is configured to, during receive operations where the unipolar transmitter ended in the relatively high state, close the first high voltage switch, open the second high voltage switch, and open the first and second low voltage switches, and wherein the controller is configured to, during receive operations where the unipolar transmitter ended in the relatively low state, close the second high voltage switch, open the first high voltage switch, and open the first and second low voltage switches.

9. The transmit and receive system of claim 1 wherein the first and second signal paths have alternating current coupled capacitors.

10. The transmit and receive system of claim 9 wherein the first and second signal paths have first and second low voltage switches between the alternating current coupled capacitors and the receiver, and wherein the controller is configured to open the first low voltage switch and close the second low voltage switch where the unipolar transmitter ends on the relative low state and is configured to open the second low voltage switch and close the first low voltage switch where the unipolar transmitter ends on the relatively high state.

11. The transmit and receive system of claim 9 further comprising:
an image processor configured to compensate for mismatch between the alternating current coupled capacitors in signals output from the receiver.

12. A transmit and receive circuit for ultrasound, the transmit and receive circuit comprising:
a unipolar transmitter configured to provide a waveform to a transducer element;
a receive amplifier; and
first and second receive paths configured to receive signals from the transducer element and connected with an input to the receive amplifier, the first and second receive paths comprise first and second capacitors, respectively.

13. The transmit and receive circuit of claim 12 wherein the unipolar transmitter is configured to connect to a single power supply.

14. The transmit and receive circuit of claim 12 wherein the first and second receive paths are configured to connect with an electrode of an element, and wherein the unipolar transmitter is configured to connect with the electrode.

15. A transmit and receive circuit for ultrasound, the transmit and receive circuit comprising:
a unipolar transmitter;
a receive amplifier;
first and second receive paths connected with an input to the receive amplifier
a power source input, a ground connector, and a transducer element connector;
wherein the unipolar transmitter includes first and second high voltage transistors and first and second low voltage transistors, the first high voltage transistor and the first low voltage transistor connected in series between the transducer element connector and the power source input, the second high voltage transistor and the second low voltage transistor connected in series between the transducer element connectors and the ground connector, the first receive path connected between the first high voltage transistor and the first low voltage transistor, the second receive path connected between the second high voltage transistor and the second low voltage transistor.

16. A method for receiving pulse inversion signals in ultrasound, the method comprising:
generating, with a unipolar pulser, first and second transmit waveforms in sequence, the first transmit waveform ending with a first voltage state and the second transmit waveform ending with a second voltage state different than the first voltage state;
routing a first receive signal responsive to the first transmit waveform along a first path from an element to a receive amplifier;
routing a second receive signal responsive to the second transmit waveform along a second path from the element to the receive amplifier; and
selecting the routing along the first and second paths based on the first and second voltage states.

17. The method of claim 16 wherein routing along the first path comprises shifting a direct current level while preserving alternating current.

18. The method of claim 16 wherein routing along the first and second paths comprises routing with transistors of the unipolar pulser during receive operation.

19. The transmit and receive circuit of claim 15 wherein the first and second low voltage transistors are configured to be opened during receive operation,
wherein the first high voltage transistor is configured, during the receive operation, to be closed when the unipolar transmitter ends a transmission in a first state and open when the unipolar transmitter ends the transmission in a second state; and
wherein the second high voltage transistor is configured, during the receive operation, to be open when the unipolar transmitter ends the transmission in the first state and closed when the unipolar transmitter ends the transmission in the second state.

20. The transmit and receive circuit of claim 15 wherein the first and second receive paths comprise first and second capacitors, respectively.

* * * * *